(12) United States Patent
Shurtliff et al.

(10) Patent No.: US 7,074,561 B2
(45) Date of Patent: Jul. 11, 2006

(54) ISOTHERMAL AMPLIFICATION BASED ASSAY FOR THE DETECTION AND QUANTITATION OF ALPHA-FETOPROTEIN MRNA

(75) Inventors: Roxanne N. Shurtliff, Herndon, VA (US); Eun Mi Lee, Rockville, MD (US)

(73) Assignee: bioMerieux, Inc., Durham, NC (US)

( * ) Notice: Subject to any disclaimer, the term of this patent is extended or adjusted under 35 U.S.C. 154(b) by 651 days.

(21) Appl. No.: 10/277,645

(22) Filed: Oct. 22, 2002

(65) Prior Publication Data

US 2004/0076962 A1 Apr. 22, 2004

(51) Int. Cl.
*C12Q 1/68* (2006.01)
*C12P 19/34* (2006.01)
*C07H 21/04* (2006.01)

(52) U.S. Cl. .................. 435/6; 435/91.2; 435/810; 536/22.1; 536/24.3

(58) Field of Classification Search .................. 435/6, 435/91.2, 810; 536/22.1, 24.3
See application file for complete search history.

(56) References Cited

U.S. PATENT DOCUMENTS

| 5,409,818 | A | 4/1995 | Davey et al. |
| 5,554,516 | A | 9/1996 | Kacian et al. |
| 5,554,527 | A | 9/1996 | Fickenscher |
| 6,093,542 | A | 7/2000 | Romano et al. |
| 6,121,023 | A | 9/2000 | Romano et al. |

FOREIGN PATENT DOCUMENTS

| DE | 195 09 169 A1 * | 9/1996 |
| EP | 0408295 | 8/1996 |
| WO | 88/10315 | 12/1998 |

OTHER PUBLICATIONS

Wong et al. "Circulating Tumor Cell mRNAs in Peripheral Blood from Hepatocellular Carcinoma Patients Under Radiotherapy, Surgical Resection or Chemotherapy: A Quantitative Evaluation," *Cancer Letters, vol.* 167, pp. 183-191 (2001).

Wong et al. "Hematogenous Dissemination of Hepatocytes and Tumor Cells after Surgical Resection of Hepatocellular Carcinoma: A Quantitative Analysis," *Clincal Cancer Research*, vol. 5, pp. 4021-4027 (1999).

Jiang et al., "Detection of Alphafetoprotein-Expressing Cells in the Blood of Patients with Hepatoma and Hepatitis," *British Journal of Cancer*, vol. 75(6), pp. 928-933 (1997).

Wong et al., "Quantitative Comparison of Alpha-Fetoprotein and Albumin mRNA Levels in Hepatocellular Carcinoma/ Adenoma, Non-tumor Liver and Blood: Implications in Cancer Detection and Monitoring," *Cancer Letters, vol.* 156, pp. 141-149 (2000).

Poon et al., "Application of Classification Tree and Neural Network Algorithms to the Identification of Serological Liver Marker Profiles for the Diagnosis of Hepatocellular Carcinoma," *Oncology*, vol. 61, pp. 275-283 (2001).

* cited by examiner

*Primary Examiner*—Kenneth R. Horlick
*Assistant Examiner*—Joyce Tung
(74) *Attorney, Agent, or Firm*—Samir R. Patel, Esq.

(57) ABSTRACT

The present invention is directed to isothermal transcription based assays for the detection and quantification of alpha-fetoprotein (AFP) mRNA. The present invention is also directed to oligonucleotides for amplifying AFP mRNA and probes for use in the detection and quantification of the amplification product. The present invention is also directed to detecting hepatocellular carcinoma, metastasis thereof and tumor recurrence by analyzing peripheral blood for the presence of AFP mRNA.

19 Claims, 1 Drawing Sheet

ISOTHERMAL AMPLIFICATION BASED ASSAY FOR THE DETECTION AND QUANTITATION OF ALPHA-FETOPROTEIN MRNA

FIELD OF THE INVENTION

The present invention relates to isothermal transcription based assays for the detection and quantitation of alpha-fetoprotein (AFP) mRNA. The present invention also relates to oligonucleotides for amplifying AFP mRNA.

BACKGROUND OF THE INVENTION

In spite of numerous advances in medical research, cancer remains as one of the leading causes of death in the United States. In industrialized nations, roughly one in five persons will die of cancer. Hepatocellular carcinoma (HCC) is one of the most common cancers in the world. The only hope for long-term survival for HCC patients is surgical resection or liver transplantation. See Wong et al., "Circulating Tumor Cell mRNAs in Peripheral Blood From Hepatocellular Carcinoma Patients Under Radiotherapy, Surgical Resection or Chemotherapy: A Quantitative Evaluation," *Cancer Letters*, 167: 183–191 (2001). However, only a minority of HCC patients are cured by removal of the tumor either by resection or transplantation and for the majority of patients, the current treatments remain unsatisfactory and the prognosis is poor. Further, more than half of those who apparently undergo successful resection subsequently develop recurrence. See Wong et al., supra, and Wong et al., "Hematogenous Dissemination of Hepatocytes and Tumor Cells After Surgical Resection of Hepatocellular Carcinoma: A Quantitative Analysis," *Clinical Cancer Research*, 5: 4021–4027 (1999).

Alpha-fetoprotein is a glycoprotein that is normally expressed during embryogenesis. It is primarily expressed in liver cells, as well as in the gut, stomach, trophoblast, lungs and pancreas. The concentration of AFP in serum decreases as the liver develops and matures. AFP levels, though, can become elevated in some disease states, particularly in HCC. See Jiang et al., "Detection of Alphafetoprotein-expressing Cells in the Blood of Patients with Hepatoma and Hepatitis," *British Journal of Cancer*, 75(6): 928–933 (1997). As such, elevated serum AFP levels have been employed as a highly specific and sensitive marker for the diagnosis of HCC. See Jiang et al., supra. Further, it has recently been found that substantially elevated levels of AFP mRNA in circulating blood are associated with recurrence or metastasis of HCC. See Wong et al., "Quantitative Comparison of Alpha-fetoprotein and Albumin mRNA Levels in Hepatocellular Carcinoma/Adenoma, Non-tumor Liver and Blood: Implications in Cancer Detection and Monitoring," *Cancer Letters*, 156: 141–149 (2000).

Survival after the onset of symptoms of HCC is only a few months and therefore, it is important to establish techniques for the early diagnosis of HCC. As HCC patients have been shown to have elevated levels of AFP mRNA, an exemplary assay for detecting the presence and level of AFP mRNA is certainly important in the diagnosis and treatment of HCC.

Currently, there are various assays on the market to detect alpha-fetoprotein such as enzyme-linked immunosorbant assay (ELISA). However, there are problems with assays such as ELISA. For instance, with ELISA, the protein level does not always correlate with the clinical stage of HCC. Molecular biological techniques such as RT-PCR assays have also been developed. However, with such biological techniques, thermal cyclers are necessary and DNA contamination is a concern.

The present invention provides for the use of isothermal nucleic acid sequence based amplification (NASBA) which is far more advantageous than an RT-PCR assay. In particular, NASBA is an isothermal amplification process and therefore, thermal cyclers are not necessary. Further, NASBA is specific for RNA and thus, DNA contamination is not a concern.

In addition, an isothermal transcription based amplification method, as compared to RT-PCR or other amplification methods, requires few manipulations by the experimenter since it is essentially isothermal. The method may be used on purified or semi-purified RNA extracts, or on cell or tissue samples with in situ amplification. Additionally, if the sample contains both DNA and RNA, the use of RT-PCR requires a first step of DNase treatment, or some method to distinguish the amplification products of mRNA- and DNA-derived PCR products is necessary. DNase treatment prior to RT-PCR can be employed (Bitsch et al., *J. Infect. Dis.* 167: 740–743 (1993); Meyer et al., *Mol. Cell Probes*, 8: 261–271 (1994)), but it sometimes fails to remove contaminating DNA sufficiently (Bitsch et al., supra).

An isothermal amplification method for the detection or quantitation of AFP mRNA has not been described. Thus, there is a need in the art for an isothermal amplification method to detect the presence of AFP mRNA and hence detect HCC, metastasis thereof and cancer recurrence.

SUMMARY OF THE INVENTION

The present invention provides for isothermal transcription based amplification assays for the detection and quantitation of AFP mRNA. In particular, the present invention provides for a method for the detection or quantitation of alpha-fetoprotein (AFP) mRNA in a sample, including the following steps:

(a) obtaining a sample which may contain AFP mRNA;

(b) performing isothermal transcription based amplification on the sample with two oligonucleotide primers, a first primer which includes at least 10 consecutive nucleotides of a sequence selected from the group consisting of SEQ ID NO: 2 and SEQ ID NO: 3, and a second primer which includes at least 10 consecutive nucleotides of a sequence selected from the group consisting of SEQ ID NO: 6 and SEQ ID NO: 7; and (c) detecting or quantitating the amplification product of step (b) whereby detection or quantitation of the amplification product indicates the presence or quantity of AFP mRNA in the sample.

The sample used may be various body tissues or cells, or cells cultured in vitro from humans or other animals. In many cases, the sample is peripheral blood or cells obtained from lymph nodes. Preferably, the sample includes cells and RNA is extracted from the cells in the sample prior to step (b).

The isothermal transcription based amplification is preferably nucleic acid sequence based amplification (NASBA). Further, it is preferable that the first primer also includes a RNA polymerase promoter sequence operably attached to the 5' end thereof. The RNA polymerase promoter sequence is preferably a T7 RNA polymerase promoter as set forth in SEQ ID NO: 1.

Step (c) in this method is preferably carried out by using a labeled wild-type probe including a sequence according to SEQ ID NO: 8 whereby hybridization of the wild-type probe to the amplification product indicates the presence of AFP mRNA in the sample. It is further preferable that a known amount of control RNA Q is added prior to step (b) and the amplification product of Q is detected by using a labeled probe including the sequence of SEQ ID NO: 10, whereby the quantity of AFP mRNA in the sample is calculated by comparing the signals of the probes for Q and the wild-type probe.

Alternatively, step (c) in this method can be carried out by using a labeled wild-type probe including a sequence according to SEQ ID NO: 8 and a capture probe according to SEQ ID NO: 9 whereby hybridization of the wild-type probe to the amplification product indicates the presence of AFP mRNA in the sample.

The present invention also provides oligonucleotides as set forth in SEQ ID NO: 2, SEQ ID NO: 3, SEQ ID NO: 6, SEQ ID NO: 7, SEQ ID NO: 8, SEQ ID NO: 9 and SEQ ID NO: 10. SEQ ID NO: 2, SEQ ID NO: 3, SEQ ID NO: 6 and SEQ ID NO: 7 are preferred oligonucleotides.

In addition, the present invention provides for an oligonucleotide of about 15–26 nucleotides, including at least 10 consecutive nucleotides of a sequence selected from the group consisting of SEQ ID NO: 2, SEQ ID NO: 3, SEQ ID NO: 6, SEQ ID NO: 7, SEQ ID NO: 8, SEQ ID NO: 9 and SEQ ID NO: 10. The oligonucleotide is preferably selected from the group consisting of SEQ ID NO: 2, SEQ ID NO: 3, SEQ ID NO: 6 and SEQ ID NO: 7. More preferably, the oligonucleotide is selected from the group consisting of SEQ ID NO: 2 and SEQ ID NO: 3, and the oligonucleotide further includes a RNA polymerase promoter sequence operatively attached to the 5' end thereof. The RNA polymerase promoter sequence is preferably a T7 RNA polymerase promoter as set forth in SEQ ID NO: 1.

Further, the present invention provides for a pair of oligonucleotides for the detection or quantitation of AFP mRNA. The first oligonucleotide of the pair is about 15–26 nucleotides in length and includes at least 10 consecutive nucleotides of a sequence selected from the group consisting of SEQ ID NO: 2 and SEQ ID NO: 3. Preferably, the first oligonucleotide includes a RNA polymerase promoter sequence operably attached to the 5' end thereof and the RNA polymerase promoter sequence is preferably a T7 RNA polymerase promoter as set forth in SEQ ID NO: 1. The second oligonucleotide of the pair is about 15–26 nucleotides in length and includes at least 10 consecutive nucleotides of a sequence selected from the group consisting of SEQ ID NO: 6 and SEQ ID NO: 7.

The present invention also provides for a primer pair for the detection or quantitation of AFP mRNA in a sample. The primer pair includes a first primer selected from the group consisting of SEQ ID NO: 2 and SEQ ID NO: 3 and a second primer selected from the group consisting of SEQ ID NO: 6 and SEQ ID NO: 7. Preferably, the first primer further includes a RNA polymerase promoter sequence operably attached to the 5' end thereof. The RNA polymerase promoter sequence is preferably a T7 RNA polymerase promoter as set forth in SEQ ID NO: 1.

In addition, the present invention provides for a kit for the detection or quantitation of AFP mRNA in a sample. The kit includes the primer pair defined above and at least one probe selected from the group consisting of SEQ ID NO: 8 and SEQ ID NO: 10. It is preferable that the kit also include a capture probe according to SEQ ID NO: 9.

The present invention also provides for another kit for the detection or quantitation of AFP mRNA in a sample. The kit includes a pair of oliogonucleotides. The first oligonucleotide of the pair is about 15–26 nucleotides in length and includes at least 10 consecutive nucleotides of a sequence selected from the group consisting of SEQ ID NO: 2 and SEQ ID NO: 3. The second oligonucleotide of the pair is about 15–26 nucleotides in length and includes at least 10 consecutive nucleotides of a sequence selected from the group consisting of SEQ ID NO: 6 and SEQ ID NO: 7.

The presence and level of AFP mRNA in a sample can be detected or quantitated by the present invention. The presence and level of AFP mRNA correlates with disease progression and is therefore useful information in the prognosis and/or management of HCC.

DETAILED DESCRIPTION OF THE INVENTION

An isothermal transcription based assay is used for the detection and quantitation of AFP mRNA. Amplification in an isothermal transcription based amplification system is achieved through the coordinated activities of three enzyme activities (reverse transcriptase, RNase H and RNA polymerase) and two DNA oligonucleotides (referred to herein as primers) specific for the target sequence. The isothermal amplification method starts with a RNA template and alternately synthesizes DNA and RNA. Using a RNA template, a primer and reverse transcriptase, a RNA/DNA hybrid is generated. The RNA is degraded from the hybrid by the RNase H activity. A double stranded DNA is then generated by reverse transcriptase using another primer, and then the double stranded DNA is used as a template for large amounts of RNA synthesis by the RNA polymerase. One of the primers has, in addition to the sequences complementary to the template, additional sequences necessary for generating a RNA polymerase promoter and transcription initiation site which can be used by the RNA polymerase. The single stranded RNA product can be readily detected through the hybridization of an appropriately labeled oligonucleotide DNA probe, with or without an additional probe which can be used to immobilize the amplification product. Detection of an amplification product indicates that the target molecule (RNA) is present in the sample, and detection of specific quantities of amplification product indicate target molecules present in the sample in specific amounts.

Any isothermal transcription based assay may be used with the primers and probes of the present invention. The isothermal transcription based assay of the present invention is carried out under conditions that can be readily determined by a person of ordinary skill in the art.

The preferred amplification method of the present invention is the isothermal transcription based amplification system referred to as NASBA. The NASBA method is disclosed in U.S. Pat. Nos. 5,409,818 and 5,554,527, each of which are herein incorporated by reference. NASBA includes the use of a T7 RNA polymerase to transcribe multiple copies of RNA from a template including a T7 promoter. Additional NASBA assays are also disclosed in U.S. Pat. Nos. 6,093,542 and 6,121,023, each of which is herein incorporated by reference.

Another technique for the amplification of a nucleic acid is the so-called transcription based amplification system (TAS). The TAS method is described in an International Patent Application, PCT Publication No. WO 88/10315, which is herein incorporated by reference. Transcription based amplification techniques usually comprise treating a target nucleic acid with two oligonucleotides, one of which comprises a promoter sequence to generate a template including a functional promoter. Multiple copies of RNA are transcribed from the template and can serve as a basis for further amplification.

Other transcription based amplification techniques are described in European Patent Application No. 408295 ("EP 408295") which is herein incorporated by reference. EP 408295 is primarily concerned with a two-enzyme transcription based amplification method. Transcription based amplification methods, such as the NASBA method described in European Patent Application No. 329822 which is herein incorporated by reference, are usually employed with a set of oligonucleotides, one of which is provided with a promoter sequence that is recognized by an enzyme with DNA dependent RNA polymerase activity such as, for example, T7 polymerase. Several modifications of transcription based techniques are known in the art. These modifications comprise, for example, the use of blocked oligonucleotides (that may be provided with a promoter sequence). These oligonucleotides are blocked so as to inhibit an extension reaction proceeding therefrom (See U.S. Pat. No. 5,554,516 which is incorporated herein by reference). One or more "promoter-primers" (oligonucleotides provided with a promoter sequence) may be used in transcription based amplification techniques, optionally combined with the use of one or more oligonucleotides that are not provided with a promoter sequence.

The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may constitute alternative structures such as "PNA" (molecules with a peptide-like backbone instead of the phosphate sugar backbone of normal nucleic acid) or the like. It is evident that these alternative structures, representing the sequences of the present invention, are likewise part of the present invention.

The term "primer" as used herein refers to an oligonucleotide either naturally occurring (e.g., as a restriction fragment) or produced synthetically, which is capable of acting as a point of initiation of synthesis of a primer extension product which is complementary to a nucleic acid strand (template or target sequence) when placed under suitable conditions (e.g., buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least 10 nucleotides in length of a sequence substantially complementary or homologous to the target sequence, but somewhat longer primers are preferred. Usually primers contain about 15–26 nucleotides but longer primers may also be employed, especially when the primers contain additional sequences such as a promoter sequence for a particular polymerase.

Normally, a set of primers will consist of at least two primers, one "upstream" (P2) and one "downstream" (P1) primer which together define the amplificate (the sequence that will be amplified using the primers). One of the primers is understood to contain, in addition to sequences that will hybridize to the target sequence, sequences which provide promoter activity. The promoter sequences are operably attached to the 5' end of the primer sequence. Most often the P1 primer will include the promoter sequence.

The term "promoter sequence" defines a region of a nucleic acid sequence that is specifically recognized by a RNA polymerase that binds to a recognized sequence and initiates the process of transcription by which a RNA transcript is produced. In principle, any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Their function as a primer, e.g., the starting point for an elongation reaction, however, may be blocked, as already mentioned above, or absent in some embodiments of transcription based amplification reactions. A particularly preferred promoter sequence is the sequence of the T7 RNA polymerase promoter, the sequence of which is as follows:

AATTCTAATACGACTCACTATAGGG (SEQ ID NO: 1)

SEQ ID NOs 4 and 5 below comprise the sequences of the specific target primer operably linked to the T7 promoter sequence shown above as SEQ ID NO: 1. This makes the sequences especially suitable for use as a downstream primer in a transcription based amplification technique such as NASBA.

A preferred embodiment of the present invention is a combination of two oligonucleotides according to the invention for use as a set in nucleic acid amplification. One of the oligonucleotides may serve as an "upstream oligonucleotide," i.e., upstream primer, while the second oligonucleotide serves as a "downstream oligonucleotide," i.e., downstream primer, in the amplification reaction.

Preferably, the reverse transcriptase activity is provided by avian myeloblastosis virus (AMV) reverse transcriptase and the RNA polymerase is provided by T7 RNA polymerase.

One of the advantages of an isothermal transcription based amplification method, as compared to other amplification methods such as PCR, is that by being essentially isothermal, it requires few manipulations by the experimenter. However, the absence of a high temperature step does make it somewhat more difficult to find appropriate primers (see below).

The amplification method of the present invention may be applied to extracts of samples comprising nucleic acid, or whole cells or tissues for in situ amplification. The samples may be various body fluids, particularly blood, plasma, and serum, from humans. The samples may also be tissue samples from humans, for instance, lymph tissue.

If the method is applied to extracts of samples comprising nucleic acids, the sample may be total RNA extracts (such as those described in Chomczynski and Sacchi, *Anal. Biochem.*, 162: 156 (1987), which is herein incorporated by reference) or "Boom" extracts (See Boom et al., *J. Clin. Micro.*, 28: 495–503 (1990), which is herein incorporated by reference). The method is preferably applied to "Boom extracts."

The amplificate is detected by hybridization with an appropriately labeled oligonucleotide probe. The label may contain a radioactive moiety, a detectable enzyme or any other moiety capable of generating a detectable signal such as a colorimetric, fluorescent, chemiluminescent or electro-chemiluminescent (ECL) signal. Blot based hybridization analysis and liquid hybridization based ECL analysis are preferably used although other analysis systems such as ELGA (enzyme-linked gel assay) and in situ hybridization can also be used.

In one embodiment of the present invention, the amplification products are resolved by agarose gel electrophoresis, then transferred to nylon membranes and hybridized to a probe that is 5'-end labeled with $^{32}$P using standard methods. The products are then visualized by autoradiography. In a second embodiment of the present invention, the amplification products can be detected using the ELGA. In this method, a probe that is specific for the amplification reaction product and conjugated at its 5' end with horseradish peroxidase (HRP) is hybridized to the amplification product. The hybridization product is then resolved electrophoretically on a polyacrylamide gel. A calorimetric enzyme reaction allows for the visualization of the reaction product in the gel. A third embodiment of the present invention makes use of electrochemiluminescence chemistry (or ECL). This embodiment uses a biotinylated capture probe immobilized onto the surface of a streptavidin-coated magnetic bead via the biotin-avidin interaction. This system also requires an oligonucleotide detector probe which can hybridize to an independent region of the amplification product. This detector probe is labeled with ruthenium, the substance that is responsible for generating an ECL signal.

The quantitative method of the present invention may use one or more internal controls to monitor the efficiency of the extraction process and the amplification assay itself. The detection systems are described in detail in Romano et al., *DNA Technology,* 16: 89–103 (1996), and Van Gemen et al., *J. of Virol. Methods,* 49:157–168 (1994), each of which are herein incorporated by reference. Methods for internal controls are described in Van Gemen et al., *Reviews in Medical Virology,* 5: 205–211 (1995), which is herein incorporated by reference.

In a preferred embodiment of the quantitative assay of the present invention, known amounts of in vitro transcribed Q RNA are spiked into the samples prior to RNA extraction, and are thereafter subjected to the same extraction and amplification procedures as the samples themselves. The Q probe is used to detect the Q amplification product and the wild-type probe is used to detect the amplification product of the AFP mRNA in the sample. The amount of signal from the Q amplification is then compared to the amount of signal from the wild-type amplification product to determine the amount of AFP mRNA present in the sample.

It may also be relevant to adapt the assay for an in situ format, which would be useful in pathology studies of tissue, particularly for lymphatic tissues. If the method is to be practiced on fixed preparations for in situ analysis, the method is performed as follows. Samples may include various body fluids or tissue samples. Lymph tissue is a preferred tissue for in situ analysis. The cells are fixed and then permeabilized to optimize permeability of the cell membranes. The fixatives are those standardly used in the art for cell or tissue preparations, such as acetone and methanol, ethanol, formalin, formaldehyde, paraformaldehyde or Permafix.RTM., and the permeabilization is done by proteinases such as proteinase K or pepsinogen. The cells are then washed to remove all reagents that might inhibit the transcription based reaction. Permeabilization is done to the point that the cells allow entry of all necessary amplification reaction components, yet retain the targets and amplification products within the cells. In addition, co-solvents such as glycerol or DMSO may be added to optimize the NASBA reaction.

Detection of amplification products can be by direct labelling (with, for instance, biotin or digoxigenin-UTP) or by in situ hybridization with a labelled probe. The direct labelling method requires that conditions can be optimized to remove an unincorporated label while maintaining the amplification products.

In a particularly preferred embodiment of the present invention, the isothermal transcription based amplification method is used in concert with a particular RNA extraction technique ("Boom extraction", Boom et al., supra), and ECL detection (electrochemiluminescence). The advantages of the system are those associated with an amplification based assay capable of providing sequence level data. Although some of these same advantages exist for the RT-PCR (i.e., increased sensitivity over ELISA, gene sequence specificity), there are advantages of NASBA for RNA over RT-PCR. These include isothermal amplification, incorporation of reverse transcription into the amplification, application to a wider array of specimen types (via Boom extract), and the sensitivity and dynamic range of the ECL detection.

Boom extracts are purified preparations of DNA and RNA. The Boom method is based on the lysing and nuclease inactivating properties of the chaotropic agent guanidinium thiocyanate (GuSCN) together with the nucleic acid binding properties of silica particles or diatoms. By using size fractionated silica particles, nucleic acids, including covalently closed circular, relaxed circular, linear double-stranded DNA, single stranded DNA, tRNA, mRNA and rRNA, can be purified from a sample in less than one hour and recovered in the original reaction vessel.

A small sample is pipetted into a reaction vessel containing a solid nucleic acid carrier and a GuSCN containing lysis buffer. Lysis of the cells occurs and the released nucleic acids bind to the carrier. The carrier-nucleic acid complexes can be separated by centrifugation. Several wash steps follow and the complexes are then dried. The nucleic acids are eluted in an aqueous low-salt buffer in the initial reaction vessel and used for the amplification reaction.

In a preferred embodiment of the present invention, a 20 µl amplification reaction is comprised of 40 mM Tris pH 8.5; 12 mM MgCl$_2$; 70 mM KCl; 5 mM DTT; 1 mM each of dATP, dCTP, dGTP and dTTP; 2 mM each of ATP, CTP and UTP; 1.5 mM GTP; 0.5 mM ITP; 15% DMSO; 0.2 µM of each oligonucleotide P1 and P2; 1.5 M Sorbitol; 2.1 µg BSA; 0.08 units RNase H; 32 units T7 RNA Polymerase; and 6.4 units AMV-RT. The 20 µl amplification reaction consists of 5 µl of the nucleic acid extract, 10 µl of premix and 5 µl of enzyme mix. (The enzyme mixture must not be vortexed). If the nucleic acid sample decreases (5 µl), then the water volume increases accordingly so that the total volume stays at 15 µl when the nucleic acid is added.

The method can be carried out as follows:
1. Mix premix.
2. Add 10 µl of premix to 5 µl of nucleic acid in an EPPENDORF tube.
3. Incubate at 65° C. for 5 minutes.
4. Transfer to 41° C. heat block, incubate for 5 minutes.
5. Add 5 µl of enzyme mix.
6. Mix without vortexing.
7. Incubate at 41° C. for 5 minutes.
8. If the tops of the tubes have condensation from the cooling, they may be spun.
9. Incubate at 41° C. for 90 minutes.
10. Spin down samples and store at −20° C.

A technical challenge encountered in the development of NASBA assays is the selection of primers. It has often been the case that primers selected from sequence data and meeting all the known requirements for primers, do not actually function in practice. In addition, in some cases, primers have been developed using model systems such as in vitro transcribed RNA, virus stocks or cell lines with very high expression of the target gene, but those primers were found to be nonfunctional when the target molecule is in a background of clinical samples. The exact mechanism underlying this problem is not understood, but is believed to arise due to the lower temperature of the NASBA reaction, which does not entirely melt the secondary structure of the target molecule and/or allows nonspecific binding of primers to background nucleic acids in the sample. It is essential for the application of the NASBA system to clinical samples that the primers not be absorbed by background nucleic acids, but rather be available for specific binding to the target molecule. The problem is encountered by the inability of the low NASBA temperature to relax secondary structure in the template RNA, making proper primer annealing even more difficult. Thus, actual primers can only be developed by means of empirical investigation and the fundamental nature of the NASBA process (i.e. low temperature) prevents accurate prediction of functional primer sets.

In the method of the present invention, primers and probes were designed for the transcript of AFP mRNA. The primer and probe sequences were derived from the Genbank entries for this gene. (Accession No. NM_001134) A total of four primers were initially designed and synthesized; there were four primer combinations (P1A and P2A ("AA"); P1A and P2B ("AB"); P1B and P2A ("BA"); and P1B and P2B ("BB")) for the target sequences. The primers and probes are listed in Table 1 below.

EXAMPLE 1

NASBA—Initial Evaluation

Two P1 and two P2 primers were designed for the AFP template as listed in Table 1 above. RNA was extracted by the method of Chomczynski and Sacchi from a hepatocellular carcinoma cell line, Hep 3B. Four possible combinations of the primers, AA, AB, BA and BB, were used in standard NASBA reactions with 5 ng of total RNA.

Amplification was achieved in a 20 μl reaction containing 5 μl of the nucleic acid extract material, 10 μl of premix and 5 μl of enzyme mix. The 20 μl amplification reaction was comprised of 40 mM Tris pH 8.5; 12 mM $MgCl_2$; 70 mM KCl; 5 mM DTT; 1 mM each of dATP, dCTP, dGTP and dTTP; 2 mM each of ATP, CTP and UTP; 1.5 mM GTP; 0.5 mM ITP; 15% DMSO; 0.2 μM of each oligonucleotide P1 and P2; 1.5 M Sorbitol; 2.1 μg BSA; 0.08 units RNase H; 32 units T7 RNA Polymerase; and 6.4 units AMV-RT.

The NASBA products were detected using ECL detection with the capture probe and the wild-type (WT) detection probe. The results are shown below in Table 2.

TABLE 1

Alpha-fetoprotein Oligonucleotides

| Oligo | *Map Position | **Sequence | |
|---|---|---|---|
| T7 Overhang | NA | AATTCTAATACGACTCACTATAGGG | (SEQ ID NO:1) |
| P1A | 583–607 | GGAAGCATTCAACTGCATTTTCAGC | (SEQ ID NO:2) |
| P1B | 650–674 | GCACATGCATGTTGATTTAACAAGC | (SEQ ID NO:3) |
| P1A+Pm | | *AATTCTAATACGACTCACTATAGGG*-GGAAGCATTCAACTGCATTTTCAGC | (SEQ ID NO:4) |
| P1B+Pm | | *AATTCTAATACGACTCACTATAGGG*-GCACATGCATGTTGATTTAACAAGC | (SEQ ID NO:5) |
| P2A | 405–429 | GATCCCACTTTTCCAAGTTCCAGAA | (SEQ ID NO:6) |
| P2B | 432–456 | TGTCACAAGCTGTGAAGCATATGAA | (SEQ ID NO:7) |
| Wild-Type Probe | 537–558 | TCTTTGGGCTGCTCGCTATGAC | (SEQ ID NO:8) |
| Capture Probe | 498–519 | AGCAAGAAGGCATCCCTTCCTG | (SEQ ID NO:9) |
| Q Probe | NA | TCTTT*TCTGGCGCGTGC*ATGAC | (SEQ ID NO:10) |

*Map position corresponds to base 1 as the A in the initiator codon.
**All sequences are listed 5' to 3'

Pm indicates the T7 RNA polymerase promoter sequence (SEQ ID NO: 1) and the T7 RNA polymerase promoter sequence is shown in italics in SEQ ID NOs 4 and 5. The italicized nucleotides in the Q probe indicate the substitution with regard to the wild-type probe.

The present invention is further detailed in the following Examples which are offered by way of illustration and are not intended to limit the invention in any manner. Standard techniques well known in the art or the techniques specifically described below are utilized.

TABLE 2

| Primer Set | 5 ng Hep 3B total RNA |
|---|---|
| AA | + |
| AB | + |
| BA | + |
| BB | + |

The initial analysis indicated that all four primer combinations were functional in NASBA amplification although primer pairs AA and AB gave slightly higher ECL signals than primer pairs BA and BB.

EXAMPLE 2

The next step in evaluating the existing primer combinations was to evaluate the sensitivity. This was done by performing serial dilutions from 500 pg to 5 fg of Hep 3B total RNA. The RNA was amplified using primer sets AA, AB, BA or BB and detected by ECL detection using the capture probe and the WT detection probe. The results are shown below in Table 3.

TABLE 3

| Hep 3B Total RNA | AA | AB | BA | BB |
|---|---|---|---|---|
| 500 pg | + | + | + | + |
| 50 pg | + | + | + | + |
| 5 pg | + | + | − | + |
| 500 fg | − | − | − | − |
| 50 fg | − | − | − | − |
| 5 fg | − | − | − | − |
| water (control) | − | − | − | − |

The results in Table 3 indicate that the various AFP primer combinations used in the NASBA based method are sensitive for detecting AFP RNA.

EXAMPLE 3

The sensitivity of the AFP NASBA assay was then determined. Dilutions were made of Hep 3B cells and extracted by the Boom method (See Boom et al, supra). The extracts were then amplified using primer set AA, AB or BB, after which the amplified product was detected by the ECL detection method using the capture probe and the WT detection probe. The results are shown below in Table 4.

TABLE 4

| Hep 3B Cell Number | AA | AB | BB |
|---|---|---|---|
| $9 \times 10^3$ | + | + | + |
| $9 \times 10^2$ | + | + | + |
| $9 \times 10^1$ | + | + | + |
| $9 \times 10^0$ | + | + | + |
| water (control) | − | − | − |

The results in Table 4 show that the primer sets all exhibit similar sensitivity with dilutions of Hep 3B cells.

EXAMPLE 4

The specificity of the AFP NASBA assay was then determined. In vitro transcribed AFP WT RNA was used as a positive control and whole blood, normal human plasma and PBMC as well as various cell lines were used as negative controls. Two colorectal adenocarcinoma cell lines, HT-29 and COLO 205, were analyzed as well as a breast cancer carcinoma cell line, MCF-7, and a prostate carcinoma cell line, LNCaP. The cells were extracted by the Boom method, after which the extract was amplified using primer set AB. The amplified product was then detected by the ECL detection method using the capture probe and the WT detection probe. The results are shown below in Table 5.

TABLE 5

| Cell Number or Volume/Sample | ECL Signal Without Background Subtraction | ECL Signal With Two Times Background Subtraction |
|---|---|---|
| Assay negative (probe only-background) | 4907 | |
| 100 ul normal human whole blood | 5035 | <lower limit |
| $10^5$ normal human PBMC | 3621 | <lower limit |
| $10^5$ MCF-7 | 3836 | <lower limit |
| $10^5$ LNCaP | 3218 | <lower limit |
| $10^5$ HT-29 | 12350 | 2536 |
| $10^5$ COLO 205 | 10919 | 1105 |
| $4.5 \times 10^1$ AFP WT RNA | 2059320 | 2049506 |
| $4.5 \times 10^0$ AFP WT RNA | 1161205 | 1151391 |
| water (control) | 3592 | <lower limit |

The results show that the AFP NASBA assay is specific for its intended target. In particular, the results show that there is slight positivity in the gut associated cell lines. Typically, two times the negative assay (capture probe and WT probe only) is subtracted from each sample to establish positivity. The HT-29 and COLO 205 cell lines are just over this cut-off point for positivity.

EXAMPLE 5

A quantitative assay for AFP RNA was developed as follows. The cDNA of AFP was cloned and used for producing in vitro RNA which was then quantified for copy number using ultraviolet spectrophotometry. The cloned AFP RNA was then subjected to in vitro mutagenesis to produce the Q version to be used for the internal control and quantitation. The WT or Q in vitro RNA was then diluted and amplified using primer set AB or BB. The results are shown below in Table 6.

The Q version of AFP can be amplified using the same primer sets as used for amplifying AFP WT, but differs from AFP WT by a substitution of 12 nucleotides in the region of the detector probe. The Q RNA therefore does not hybridize to the WT probe and the WT RNA does not hybridize to the Q probe (data not shown).

TABLE 6

| | Primer Set and Template | | | |
|---|---|---|---|---|
| Input AFP RNA copies | AB: WT RNA | AB: Q RNA | BB: WT RNA | BB: Q RNA |
| $5 \times 10^5$ | + | + | + | + |
| $5 \times 10^4$ | + | + | + | + |
| $5 \times 10^3$ | + | + | + | + |
| $5 \times 10^2$ | + | + | + | + |
| $5 \times 10^1$ | + | + | + | + |
| $5 \times 10^0$ | − | − | − | − |
| water | − | − | − | − |

The results in Table 6 show that the sensitivity of the assay is approximately 50 copies for both WT and Q RNA. It is important that amplification efficiency is the same for both of the WT and Q in vitro RNA in uniplex before used in a quantitative assay where both species of RNA will be present in the same tube.

For a quantitative assay, a known amount of Q RNA was spiked into the sample and then subjected to extraction and amplification along with the sample RNA. After amplification, the products were independently probed with the WT probe and the Q probe. The amount of WT RNA present was calculated from the ratio obtained of Q signal to WT signal. This signal ratio was tested in the assay using primer set AB to amplify known quantities of in vitro transcribed WT RNA. The results are shown below in Table 7.

TABLE 7

| Input AFP WT in vitro RNA | Mean of Calculated WT RNA ( n = 3 ) |
|---|---|
| $4.5 \times 10^6$ | $4.3 \times 10^6$ |
| $4.5 \times 10^5$ | $6.0 \times 10^5$ |
| $4.5 \times 10^4$ | $6.4 \times 10^4$ |
| $4.5 \times 10^3$ | $2.1 \times 10^3$ |
| water | <lower limit |

The results in Table 7 show that AFP RNA can be quantitated using the NASBA method.

The AFP quantitative NASBA assay has also been applied to the quantitation of AFP RNA in cells. Hep 3B cells and macaque liver cells were used as template. Ten fold dilutions were made of the cells, extracted by the Boom method and amplified using the primer set AB (data not shown).

Figure 1:
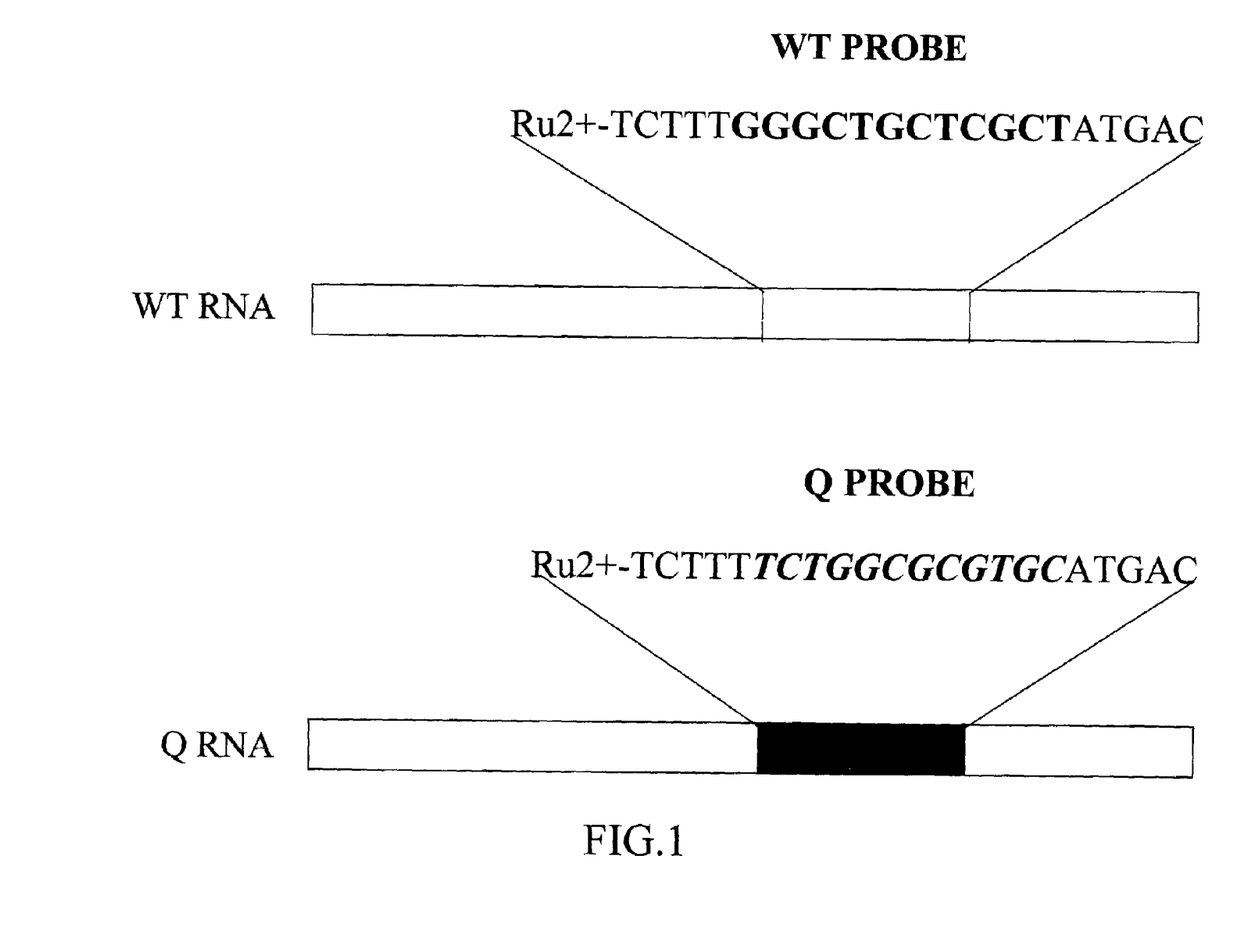
FIG. 1 shows both a wild-type RNA in which a wild-type probe is hybridized to its mutually exclusive intended target and a Q RNA in which a Q probe is hybridized to its mutually exclusive intended target.

The results in the Examples of the present application demonstrate that the primers and probes of the present invention can specifically detect low levels of target molecule, even in the background of clinical samples. In addition, the primers can amplify the Q RNA while the Q probe and WT probe hybridize to their mutually exclusive intended targets (See FIG. 1). Thus, the primers used in the present invention provide unexpectedly good results for the detection and quantitation of AFP RNA.

The publications and other materials used herein to illuminate the background of the invention and provide additional details respecting the practice of the invention are incorporated herein by reference as if each was individually incorporated herein by reference.

Thus, while there have been described what are presently believed to be the preferred embodiments of the present invention, those skilled in the art will realize that other and further embodiments can be made without departing from the spirit and scope of the invention, and it is intended to include all such further modifications and changes as come within the true scope of the invention.

What is claimed is:

1. A method for the detection or quantitation of alpha-fetoprotein (AFP) mRNA in a sample, comprising:

(a) obtaining a sample which may contain AFP mRNA;

(b) performing isothermal transcription based amplification on the sample with two oligonucleotide primers, a first primer which comprises at least 10 consecutive nucleotides of a sequence selected from the group consisting of SEQ ID NO: 2 and SEQ ID NO: 3, and a second primer which comprises at least 10 consecutive nucleotides of a sequence selected from the group consisting of SEQ ID NO: 6 and SEQ ID NO: 7; and (c) detecting or quantitating the amplification product of step (b) whereby detection or quantitation of the amplification product indicates the presence or quantity of AFP mRNA in the sample.

2. The method of claim 1, wherein detection of the amplification product uses a labeled wild-type probe comprising a sequence according to SEQ ID NO: 8, whereby hybridization of the wild-type probe to the amplification product indicates the presence of AFP mRNA in the sample.

3. The method of claim 2, further comprising adding a known amount of control RNA Q prior to step (b), and detecting amplification product of Q by using a labeled probe comprising the sequence of SEQ ID NO: 10, whereby the quantity of AFP mRNA in the sample is calculated by comparing the signals of the probes for Q and the wild-type probe.

4. The method of claim 2, wherein detection of the amplification product further uses a capture probe according to SEQ ID NO: 9.

5. The method of claim 1, wherein the sample comprises cells and RNA is extracted from the cells in the sample prior to step (b).

6. The method of claim 1, wherein the first primer further comprises a RNA polymerase promoter sequence operably attached to the 5' end thereof.

7. The method of claim 6, wherein the RNA polymerase promoter sequence is a T7 RNA polymerase promoter as set forth in SEQ ID NO: 1.

8. The method of claim 1, wherein the isothermal transcription based amplification is nucleic acid sequence based amplification (NASBA).

9. An oligonucleotide selected from the group consisting of SEQ ID NO: 2, SEQ ID NO: 3 and SEQ ID NO: 7.

10. An oligonucleotide of about 15–26 nucleotides, comprising at least 10 consecutive nucleotides of a sequence selected from the group consisting of SEQ ID NO: 2 and SEQ ID NO: 3, wherein the oligonucleotide further comprises a RNA polymerase promoter sequence operatively attached to the 5' end thereof.

11. The oligonucleotide of claim 10, wherein the RNA polymerase promoter sequence is a T7 RNA polymerase promoter as set forth in SEQ ID NO: 1.

12. A pair of oligonucleotides for the detection or quantitation of AFP mRNA, a first oligonucleotide of said pair being about 15–26 nucleotides in length and comprising at least 10 consecutive nucleotides of a sequence selected from the group consisting of SEQ ID NO: 2 and SEQ ID NO: 3, and a second oligonucleotide of said pair being about 15–26 nucleotides in length and comprising at least 10 consecutive nucleotides of a sequence selected from the group consisting of SEQ ID NO: 6 and SEQ ID NO: 7.

13. The pair of oligonucleotides of claim 12, wherein the first oligonucleotide further comprises a RNA polymerase promoter sequence operably attached to the 5' end thereof.

14. The pair of oligonucleotides of claim 13, wherein the RNA polymerase promoter sequence is a T7 RNA polymerase promoter as set forth in SEQ ID NO: 1.

15. A primer pair for the detection or quantitation of AFP mRNA in a sample, comprising a first primer selected from the group consisting of SEQ ID NO: 2 and SEQ ID NO: 3, and a second primer selected from the group consisting of SEQ ID NO: 6 and SEQ ID NO: 7.

16. The primer pair of claim 15, wherein the first primer further comprises a RNA polymerase promoter sequence operably attached to the 5' end thereof.

17. A kit for the detection or quantitation of AFP mRNA in a sample, comprising the primer pair of claim 15 and at least one probe selected from the group consisting of SEQ ID NO: 8 and SEQ ID NO: 10.

18. The kit of claim 17, further comprising a capture probe according to SEQ ID NO: 9.

19. A kit for the detection or quantitation of AFP mRNA in a sample, comprising a pair of oligonucleotides of claim 12.

* * * * *

SEQUENCE LISTING

<160> NUMBER OF SEQ ID NOS: 10

<210> SEQ ID NO 1
<211> LENGTH: 25
<212> TYPE: DNA
<213> ORGANISM: Artificial
<220> FEATURE:
<223> OTHER INFORMATION: T7 RNA Polymerase Promoter

<400> SEQUENCE: 1
aattctaata cgactcacta taggg                                    25

<210> SEQ ID NO 2
<211> LENGTH: 25
<212> TYPE: DNA
<213> ORGANISM: Artificial
<220> FEATURE:
<223> OTHER INFORMATION: Primer P1A

<400> SEQUENCE: 2
ggaagcattc aactgcattt tcagc                                    25

<210> SEQ ID NO 3
<211> LENGTH: 25
<212> TYPE: DNA
<213> ORGANISM: Artificial
<220> FEATURE:
<223> OTHER INFORMATION: Primer P1B

<400> SEQUENCE: 3
gcacatgcat gttgatttaa caagc                                    25

<210> SEQ ID NO 4
<211> LENGTH: 50
<212> TYPE: DNA
<213> ORGANISM: Artificial
<220> FEATURE:
<223> OTHER INFORMATION: Primer P1A + T7 RNA Polymerase Promoter

<400> SEQUENCE: 4
aattctaata cgactcacta tagggggaag cattcaactg cattttcagc          50

```
<210> SEQ ID NO 5
<211> LENGTH: 50
<212> TYPE: DNA
<213> ORGANISM: Artificial
<220> FEATURE:
<223> OTHER INFORMATION: Primer P1B + T7 RNA Polymerase Promoter

<400> SEQUENCE: 5
aattctaata cgactcacta tagggcaca tgcatgttga tttaacaagc         50

<210> SEQ ID NO 6
<211> LENGTH: 25
<212> TYPE: DNA
<213> ORGANISM: Artificial
<220> FEATURE:
<223> OTHER INFORMATION: Primer P2A

<400> SEQUENCE: 6
gatcccactt ttccaagttc cagaa                                   25

<210> SEQ ID NO 7
<211> LENGTH: 25
<212> TYPE: DNA
<213> ORGANISM: Artificial
<220> FEATURE:
<223> OTHER INFORMATION: Primer P2B

<400> SEQUENCE: 7
tgtcacaagc tgtgaagcat atgaa                                   25

<210> SEQ ID NO 8
<211> LENGTH: 22
<212> TYPE: DNA
<213> ORGANISM: Artificial
<220> FEATURE:
<223> OTHER INFORMATION: Wild-Type Probe

<400> SEQUENCE: 8
tctttgggct gctcgctatg ac                                      22

<210> SEQ ID NO 9
<211> LENGTH: 22
<212> TYPE: DNA
<213> ORGANISM: Artificial
<220> FEATURE:
<223> OTHER INFORMATION: Capture Probe

<400> SEQUENCE: 9
agcaagaagg catcccttcc tg                                      22

<210> SEQ ID NO 10
<211> LENGTH: 22
<212> TYPE: DNA
<213> ORGANISM: Artificial
<220> FEATURE:
<223> OTHER INFORMATION: Q Probe

<400> SEQUENCE: 10
tcttttctgg cgcgtgcatg ac                                      22
```